United States Patent [19]

Maurer

[11] Patent Number: 4,536,574
[45] Date of Patent: Aug. 20, 1985

[54] PREPARATION OF 2-ALKYLTHIOMETHYL-4-HYDROXYPYRIMIDINES

[75] Inventor: Fritz Maurer, Wuppertal, Fed. Rep. of Germany

[73] Assignee: Bayer Aktiengesellschaft, Leverkusen, Fed. Rep. of Germany

[21] Appl. No.: 559,147

[22] Filed: Dec. 7, 1983

[30] Foreign Application Priority Data

Dec. 24, 1982 [DE] Fed. Rep. of Germany ....... 3247926

[51] Int. Cl.³ .................. C07D 239/36; C07D 239/70
[52] U.S. Cl. ..................................... 544/253; 544/319; 564/225
[58] Field of Search ................. 544/253, 319; 564/225

[56] References Cited

U.S. PATENT DOCUMENTS

| | | | |
|---|---|---|---|
| 3,417,122 | 12/1968 | McManus | 564/225 |
| 3,732,305 | 5/1973 | Bauer | 564/225 |
| 4,014,879 | 3/1977 | Balke et al. | 544/319 |
| 4,018,771 | 4/1977 | Gupton et al. | 544/319 |
| 4,052,396 | 10/1977 | Pociask | 544/319 |
| 4,052,397 | 10/1977 | Blackwell et al. | 544/319 |
| 4,144,271 | 3/1979 | Jones et al. | 564/225 |
| 4,163,848 | 8/1979 | Blackwell et al. | 544/319 |
| 4,200,637 | 4/1980 | Maurer et al. | 544/319 |

FOREIGN PATENT DOCUMENTS 0022511  1/1981  European Pat. Off. .
2083814  3/1982  United Kingdom .

Primary Examiner—Donald G. Daus
Assistant Examiner—Stephen Kapner
Attorney, Agent, or Firm—Sprung, Horn, Kramer & Woods

[57] ABSTRACT

A process for preparing 2-alkylthiomethyl-4-hydroxypyrimidines, known to be useful as intermediates in making insecticides, of the formula

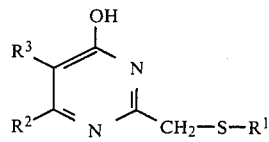

(I)

in which
$R^1$ is alkyl,
$R^2$ is hydrogen or alkyl, and
$R^3$ is hydrogen, alkyl or alkoxy, or
$R^2$ and $R^3$ together represent a divalent alkylene radical, comprising reacting a sulphonyloxyacetonitrile of the formula

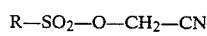

(II)

in which
R is alkyl, halogenoalkyl or optionally substituted aryl, with methanol or ethanol, reacting the reaction mixture formed with ammonium chloride, reacting the reaction mixture formed with an alkali metal thiolate of the formula

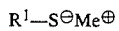

(III)

in which Me⁺ is an alkali metal cation, and, in the presence of a base, with a β-ketocarboxylic acid ester of the formula

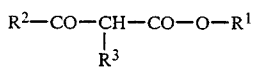

(IV)

at a temperature between about −20° and +100° C.

7 Claims, No Drawings

PREPARATION OF 2-ALKYLTHIOMETHYL-4-HYDROXYPYRIMIDINES

The invention relates to a new process for the preparation of 2-alkylthiomethyl-4-hydroxypyrimidines.

It is already known that 2-alkylthiomethyl-4-hydroxypyrimidines are obtained when 2-chloromethyl-4-hydroxypyrimidines are reacted with alkali metal thiolates (compare DE-OS (German Published Specification) No. 2,752,613 and U.S. Pat. No. 4,200,637). The disadvantage of this process is that the starting compound 2-chloromethyl-4-hydroxypyrimidine can be obtained only by an expensive synthesis via 4 stages (C.A., 71, 70563a (1969)), and that the yields of 2-alkylthiomethyl-4-hydroxypyrimidine are frequently very unsatisfactory (compare DE-OS (German Published Specification) No. 2,752,613 and DE-OS (German Published Specification) No. 2,838,359).

It is furthermore known that 2-alkylthiomethyl-4-hydroxypyrimidines are also obtained when alkylthioacetamidines are cyclized with β-ketocarboxylic acid esters (compare EP-OS (European Published Specification) No. 22,511). However, the disadvantage of this process is that the amidines used as starting substances can be obtained only in a multi-stage reaction from chloroacetonitrile (Houben Weyl, Methoden der organischen Chemie (Methods of Organic Chemistry), Volume 8, 4th edition, Thieme Verlag Stuttgart, 1952, pages 698, 699 and 702), which means that the process proceeds with relatively poor yields.

It has been found that 2-alkylthiomethyl-4-hydroxypyrimidines of the formula (I)

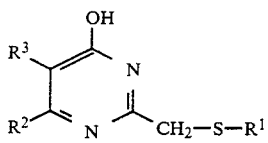
(I)

in which
R$^1$ represents alkyl,
R$^2$ represents hydrogen or alkyl and
R$^3$ represents hydrogen, alkyl or alkoxy, or
R$^2$ and R$^3$ together represent a divalent alkylene radical,
are obtained in a multi-stage process, without isolation of the intermediates, if sulphonyloxyacetonitriles of the general formula (II)

$$R-SO_2-O-CH_2-CN \qquad (II)$$

in which R represents alkyl, halogenoalkyl or optionally substituted aryl,
are reacted with methanol or ethanol, if appropriate in the presence of a diluent and if appropriate in the presence of catalytic amounts of a base, the reaction mixture formed is reacted with ammonium chloride, and the reaction mixture formed is reacted with an alkali metal thiolate of the formula (III)

$$R^1-S^\ominus Me^{\oplus} \qquad (III)$$

in which
R$^1$ has the abovementioned meaning and
Me$^\oplus$ represents an alkali metal cation, and, in the presence of a base, with a β-ketocarboxylic acid ester of the formula (IV)

$$R^2-CO-\underset{\underset{R^3}{|}}{CH}-CO-O-R^1 \qquad (IV)$$

in which
R$^2$ and R$^3$ have the abovementioned meaning and
R$^1$ represents alkyl,
at temperatures between −20° and +100° C.

It is to be regarded as decidedly surprising that the desired 2-alkylthiomethyl-4-hydroxypyrimidines are obtained in good yields with the aid of the process according to the invention, since the individual stages known from the prior art for the preparation of 2-alkylthiomethyl-4-hydroxypyrimidines as a rule give only unsatisfactory yields. It could not be expected that the 2-alkylthiomethyl-4-hydroxypyrimidines are obtained in a good yield and purity via 4 stages without isolation and purification of the intermediates.

Those compounds of the formula (I)
in which
R$^1$ represents straight-chain or branched alkyl with up to 6, in particular with 1 to 4, carbon atoms,
R$^2$ represents hydrogen or straight-chain or branched alkyl with up to 6, in particular with 1 to 4, carbon atoms and
R$^3$ represents hydrogen, straight-chain or branched alkyl with up to 6, in particular with 1 to 4, carbon atoms or straight-chain or branched alkoxy with up to 6, in particular with 1 to 4, carbon atoms, or
R$^2$ and R$^3$ together represent a divalent alkylene radical with 3 to 5 carbon atoms,
are preferably obtained with the aid of the process according to the invention.

If, for example, cyanomethyl p-toluenesulphonate, sodium methylthiolate and methyl 2-methylacetoacetate are used as starting substances and sodium methylate is used as the base, the process according to the invention can be represented by the following equation:

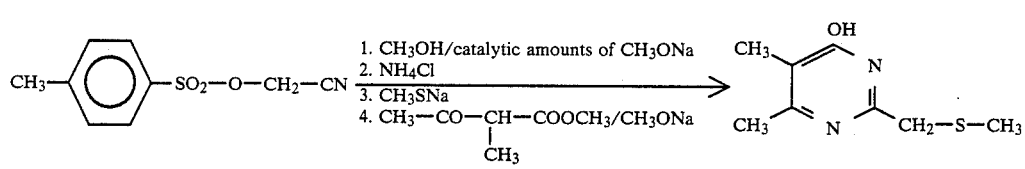

Formula (II) provides a general definition of the sulphonyloxyacetonitriles required as starting substances for carrying out the process according to the invention. In this formula, R preferably represents straight-chain or branched alkyl with up to 4 carbon atoms, straight-chain or branched halogenoalkyl with up to 10 carbon atoms and up to 21 halogen atoms, or phenyl which is optionally mono-, di- or tri-substituted by identical or different substituents from the group comprising halogen, nitro, cyano, alkyl and alkoxy with in each case up to 4 carbon atoms and halogenoalkyl with up to 2 carbon atoms and up to 5 halogen atoms. R particularly preferably represents phenyl, p-tolyl, methyl, trifluoromethyl or nonafluorobutyl. The sulphonyloxyacetonitriles of the formula (II) are known, or they can be prepared in a simple manner by known processes, by reacting sulphonyl chlorides of the formula (V)

R—SO₂—Cl  (V)

in which R has the abovementioned meaning,
with formalin and sodium cyanide (compare Bull.Soc.-Chim. France 1948, 945).

Formula (III) provides a general definition of the alkali metal thiolates also required as starting substances for carrying out the process according to the invention. In this formula, $R^1$ preferably represents straight-chain or branched alkyl with up to 6, in particular with 1 to 4, carbon atoms and $Me^\oplus$ preferably represents a sodium or potassium cation. The alkali metal thiolates of the formula (III) are generally known compounds of organic chemistry.

Formula (IV) provides a general definition of the β-ketocarboxylic acid esters also required as starting substances for carrying out the process according to the invention. In this formula, $R^2$ and $R^3$ preferably represent those radicals which have already been listed as preferred in the description of the corresponding radicals of the compounds of the formula (I). $R^1$ preferably represents straight-chain or branched alkyl with up to 4 carbon atoms. The β-ketocarboxylic acid esters of the formula (IV) are likewise generally known compounds of organic chemistry.

The process according to the invention is preferably carried out in the presence of a suitable diluent. Possible diluents are virtually all the inert organic solvents.

These include, in particular, aliphatic and aromatic, optionally chlorinated hydrocarbons, such as benzine, benzene, toluene, xylene, methylene chloride, chloroform, carbon tetrachloride, chlorobenzene and o-dichlorobenzene, ethers, such as diethyl ether and dibutyl ether, tetrahydrofuran and dioxane, and alcohols, such as methanol, ethanol and isopropanol. Alcohols, especially methanol and ethanol, are preferred.

If appropriate, the process according to the invention can be carried out in the presence of bases. All the customary organic or inorganic bases can be used as the bases.

Bases which have proved particularly suitable are alkali metal carbonates and alcoholates, such as sodium and potassium carbonate and sodium and potassium methylate and ethylate, and furthermore aliphatic, aromatic and heterocyclic amines, for example triethylamine, trimethylamine, dimethylaniline, dimethylbenzylamine and pyridine. Alkali metal alcoholates, especially alkali metal methylates and ethylates, are preferred.

The process according to the invention is in general carried out at temperatures between −20° and +100° C. The temperature range between 0° and +50° C., especially that between 0° C. and room temperature, is preferred. The reactions are in general carried out under normal pressure.

The process is carried out by first reacting the sulphonyloxyacetonitriles of the formula (II) with equimolar amounts of methanol or ethanol. Preferably, methanol or ethanol is thereby employed in excess, as the solvent. The presence of catalytic amounts of a base has proved advantageous.

Ammonium chloride is then added to the reaction mixture. 1–2 mols, preferably 1–1.2 mols, of ammonium chloride per mol of sulphonyloxyacetonitrile are employed.

After the sulphonyloxacetamidine hydrochloride resulting from these reactions has formed, the reaction mixture is either reacted first with an alkali metal thiolate and then, in the presence of a base, with a β-ketocarboxylic acid ester, or reacted first with the β-ketocarboxylic acid ester, in the presence of a base, and then with the alkali metal thiolate. Preferably, however, the reaction mixture is reacted first with the alkali metal thiolate and then with the β-ketocarboxylic acid ester.

The alkali metal thiolate can advantageously be formed in situ by first adding the corresponding amount of mercaptan (1–1.5 mols per mol of sulphonyloxyacetonitrile) to the reaction mixture and then adding the corresponding amount of a base.

The reaction with the β-keto ester is carried out in the presence of a base. 2–2.5 mols, preferably 2–2.2 mols, of base are preferably employed per mol of sulphonyloxyacetonitrile.

If diluents are used, these are distilled off in vacuo when the reaction has ended. The residue is then dissolved in water, the solution is neutralized by addition of an acid, such as, for example, hydrochloric acid, sulphuric acid, phosphoric acid, formic acid or acetic acid, and the product which has precipitated is filtered off with suction. In the case where the reaction products are soluble in water, they are isolated by extraction of the aqueous solution with a water-immiscible organic solvent, such as, for example, chlorohydrocarbons or lower carboxylic acid alkyl esters.

The compounds of the formula (I) are as a rule obtained in solid form, and can be purified by recrystallization. They are characterized by their melting point.

The 2-alkylthiomethyl-4-hydroxypyrimidines prepared with the aid of the process according to the invention are used as starting substances for highly active insecticides (compare European Publ. Spec. 22,511 and DE-OS (German Published Specification) No. 2,752,613 or U.S. Pat. No. 4,200,637).

PREPARATION EXAMPLES

Example 1

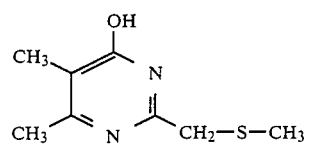

21.1 g (0.1 mol) of cyanomethyl p-toluenesulphonate are added in portions to a solution of 0.01 mol of sodium methylate in 100 ml of methanol at 0° to 5° C. The mixture is allowed to come to 20° C., 5.9 g (0.11 mol) of ammonium chloride are added at this temperature and the mixture is stirred at room temperature for 4 hours. 6 g (0.125 mol) of methylmercaptan are then passed in at 10° C., a solution of 0.11 mol sodium methylate in 20 ml of methanol is added dropwise at the same temperature, and the mixture is stirred first at 0° to 5° C. for 1 hour and then without cooling for 2 hours. A further 0.22 mol of sodium methylate in 40 ml of methanol and then 13 g (0.1 mol) of methyl 2-methylacetoacetate are added to the reaction mixture at room temperature, and the mixture is subsequently stirred at room temperature for a further 18 hours. The solvent is then distilled off in vacuo, the residue is dissolved in 100 ml of water and the solution is brought to pH 4 with concentrated hydrochloric acid at 10° to 20° C. The product which has precipitated is filtered off with suction and rinsed with 20 ml of cold water. 12.8 g (70% of theory) of 2-methylthiomethyl-4-hydroxy-5,6-dimethylpyrimidine are obtained in this manner in the form of a beige powder of melting point 166° C.

Example 2

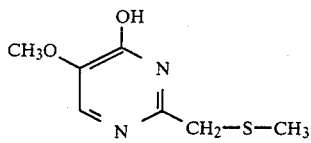

21.1 g (0.1 mol) of cyanomethyl p-toluenesulphonate are added to a solution of 0.01 mol of sodium methylate in 100 ml of methanol at 0° to 5° C. The mixture is allowed to come to 20° C., 5.9 g (0.11 mol) of ammonium chloride are added at this temperature and the mixture is subsequently stirred at room temperature for 4 hours. 6 g (0.125 mol) of methylmercaptan are then passed in at 10° C., a solution of 0.11 mol of sodium methylate in 20 ml of methanol is added dropwise at the same temperature, and the mixture is subsequently stirred first at 0° to 5° C. for 1 hour then without cooling for 2 hours. A further 0.11 mol of sodium methylate in 20 ml of methanol and then 15.4 g (0.1 mol) of the sodium salt of methyl hydroxymethylene-methoxyacetate are added to the reaction mixture at room temperature and the mixture is subsequently stirred at room temperature for a further 18 hours. The solvent is then distilled off in vacuo, the residue is dissolved in 100 ml of water and the solution is brought to pH 4 with concentrated hydrochloric acid at 10° to 20° C. The mixture is then extracted with three 100 ml portions of methylene chloride, the organic phase is dried over sodium sulphate and the solvent is distilled off in vacuo. 11.1 g (60% of theory) of 2-methylthiomethyl-4-hydroxy-5-methoxypyrimidine remain in the form of a beige powder of melting point 136° C.

The following compounds, for example, can be prepared analogously to Example 1 or 2:

| | Melting point (°C.) |
|---|---|
| 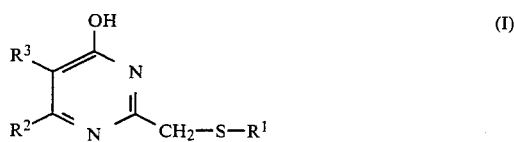 | 170 |
| | 177 (decomposition) |
| | 122 |
|  | 151 |
|  | 138 |
| 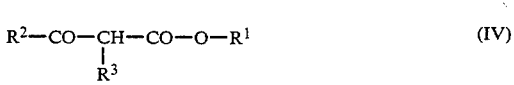 | 119 |

It will be understood that the specification and examples are illustrative but not limitative of the present invention and that other embodiments within the spirit and scope of the invention will suggest themselves to those skilled in the art.

What is claimed is:

1. A process for the preparation of a 2-alkylthiomethyl-4-hydroxypyrimidine of the formula $$\text{(I)}$$

(structure with $R^3$, $R^2$, OH, N, N, $CH_2-S-R^1$)

in which
$R^1$ is alkyl,
$R^2$ is hydrogen or alkyl, and
$R^3$ is hydrogen, alkyl or alkoxy, or
$R^2$ and $R^3$ together represent a divalent alkylene radical, comprising reacting a sulphonyloxyacetonitrile of the formula $$R-SO_2-O-CH_2-CN \quad \text{(II)}$$

in which
R is alkyl, halogenoalkyl or optionally substituted aryl, with methanol or ethanol, reacting the reaction mixture formed with ammonium chloride, reacting the reaction mixture formed with an alkali metal thiolate of the formula $$R^1-S^{\ominus}Me^{\oplus} \quad \text{(III)}$$

in which
$Me^+$ is an alkali metal cation,
and, in the presence of a base, with a β-ketocarboxylic acid ester of the formula $$R^2-CO-\underset{R^3}{CH}-CO-O-R^1 \quad \text{(IV)}$$

at a temperature between about −20° and +100° C.

2. A process according to claim 1,
in which
R$^1$ is alkyl with up to 6 carbon atoms,
R$^2$ is hydrogen or alkyl with up to 6 carbon atoms, and
R$^3$ is hydrogen, or alkyl or alkoxy with up to 6 carbon atoms, or
R$^2$ and R$^3$ together are divalent alkylene with 3 to 5 carbon atoms.

3. A process according to claim 1, carried out in methanol or ethanol as solvent.

4. A process according to claim 1, wherein the alkali metal thiolate of the formula (III) is prepared in situ.

5. A process according to claim 1, wherein an alkali metal alcoholate is used as the base.

6. A process according to claim 1, carried out at a temperature between about 0° C. and room temperature.

7. A process according to claim 2, carried out in methanol or ethanol as solvent at a temperature between about 0° C. and room temperature, wherein the alkali metal thiolate of the formula (III) is prepared in situ and an alkali metal alcoholate is used as the base.

* * * * *